(12) United States Patent
Habboushe et al.

(10) Patent No.: US 8,934,637 B2
(45) Date of Patent: Jan. 13, 2015

(54) ELECTRONIC STETHOSCOPE

(71) Applicant: Elegant Medical LLC, New Hyde Park, NY (US)

(72) Inventors: Joseph Habboushe, New Hyde Park, NY (US); Richard Derman, New Hyde Park, NY (US); Stephen Ahnert, New Hyde Park, NY (US); Scott Poff, New Hyde Park, NY (US)

(73) Assignee: Elegant Medical LLC, New Hyde Park, NY (US)

( * ) Notice: Subject to any disclaimer, the term of this patent is extended or adjusted under 35 U.S.C. 154(b) by 0 days.

(21) Appl. No.: 14/075,420

(22) Filed: Nov. 8, 2013

(65) Prior Publication Data

US 2014/0153730 A1    Jun. 5, 2014

Related U.S. Application Data

(60) Provisional application No. 61/732,788, filed on Dec. 3, 2012.

(51) Int. Cl.
*A61B 7/04*      (2006.01)
*H04R 1/46*      (2006.01)

(52) U.S. Cl.
CPC ...................................... *H04R 1/46* (2013.01)
USPC ............................................ 381/67; 181/131

(58) Field of Classification Search
USPC .............. 381/67; 600/528, 529, 300; 181/131
See application file for complete search history.

(56) References Cited

U.S. PATENT DOCUMENTS

| | | | |
|---|---|---|---|
| 2008/0037800 A1* | 2/2008 | Grasfield et al. | 381/67 |
| 2008/0137876 A1 | 6/2008 | Kassal et al. | |
| 2009/0279708 A1* | 11/2009 | Habboushe | 381/67 |
| 2011/0096936 A1* | 4/2011 | Gass | 381/67 |

FOREIGN PATENT DOCUMENTS

FR     2659007     9/1991

OTHER PUBLICATIONS

International Search Report and Written Opinion from PCT/US2013/072848, dated Apr. 3, 2014, 5 pages.

* cited by examiner

*Primary Examiner* — Paul S Kim
(74) *Attorney, Agent, or Firm* — Sheppard Mullin Richter & Hampton LLP

(57) ABSTRACT

Provided is an electronic stethoscope pick-up head comprising an acousto-electrical transducer disposed in a chamber, the transducer being configured to generate an electrical signal representing acoustical vibrations, wherein the chamber further comprises a sound influencing bell defining a cavity to provide air communication between the transducer and a diaphragm attached to an outer end of the bell, wherein the diaphragm is acoustically decoupled from the transducer; and one or more ventilation air path as the only means to provide air communication between the cavity and outside of the chamber, wherein the air path is configured to restrict air flow through the air path.

20 Claims, 5 Drawing Sheets

ELECTRONIC STETHOSCOPE

CROSS-REFERENCE TO RELATED APPLICATIONS

This application claims the benefit under 35 U.S.C. §119(e) of U.S. Application No. 61/732,788, filed Dec. 3, 2012, which application is hereby incorporated by reference in its entirety.

FIELD OF THE DISCLOSURE

The present disclosure relates generally to medical stethoscopes. More specifically, the present disclosure relates to an electronic stethoscope system and method for using the same to provide high quality sound and a more user-friendly interface, and reduce cross-infection in hospitals.

BACKGROUND

Hospital-acquired infections every year cause up to 90,000 deaths, 2 million extended hospital stays, and over $2.6 Billion in medical costs, in the U.S. alone. Research has found that up to 90% of conventional stethoscopes in a hospital carry infectious bacteria. This is especially significant for patients in intensive care units. Currently, many hospitals put a cheap disposable stethoscope bedside in intensive care units as a means of limiting patient-to-patient transmission of infections.

Clinicians often avoid using this cheap stethoscope bedside because of either poor sound quality and/or because of the discomfort to putting a stethoscope many other people may have used in their ears. Instead, some clinicians either use their own stethoscopes, breaking the isolation barrier, or perhaps worse, they avoid routine stethoscope examinations.

Efforts to reduce hospital-acquired infections, however, have generally resulted in the design of inconvenient devices, and more important perhaps, at a cost of deteriorated quality of sound.

SUMMARY

One embodiment of the disclosure provides an apparatus comprising an acousto-electrical transducer disposed in a chamber, the transducer being configured to generate an electrical signal representing acoustical vibrations, wherein the chamber further comprises a sound influencing bell defining a cavity to provide air communication between the transducer and a diaphragm attached to an outer end of the bell, wherein the diaphragm is acoustically decoupled from the transducer (or the diaphragm is acoustically coupled to the transducer); and one or more ventilation air paths as the only means to provide air communication between the cavity and outside of the chamber, wherein the air path is configured to restrict air flow through the air path.

In one embodiment provided is an apparatus comprises
a non-contact acousto-electrical transducer disposed in a chamber, the transducer being configured to generate an electrical signal representing acoustical vibrations;
a sound influencing bell formed as part of the chamber;
a diaphragm attached to an outer end of the bell, the bell defining a cavity to provide air communication between the transducer and the diaphragm, wherein the diaphragm is acoustically coupled to the transducer through the air communication. In another embodiment, the apparatus further comprises one or more ventilation air path as the only means to provide air communication between the cavity and outside of the chamber, wherein the air path is configured to restrict air flow through the air path.

In one aspect, at least a portion of the air path has a cross-sectional area of less than about 6 $mm^2$. In one aspect, the cross-sectional area is greater than about 0.5 $mm^2$. In some aspects, the cross-sectional area is between about 1 $mm^2$ and about 5 $mm^2$.

In one aspect, the cross-sectional area is adjustable. In another aspect, the air path is convoluted.

In one aspect, the transducer comprises a microphone. In another aspect, the transducer comprises an electromagnetic diaphragm.

In one aspect, the apparatus further comprises a cable for connecting the transducer to an external device. In one aspect, the external device is a speaker or an electronic screen.

In one aspect, the apparatus further comprises a wireless transmitter for transmitting an electronic signal generated by the transducer. In one aspect, the wireless transmitter is a Bluetooth or near field communication (NFC) transmitter.

In one aspect, the apparatus further comprises a flexible material for affixing the transducer in the chamber and separating the transducer from other parts of the chamber.

In one aspect, the apparatus further comprises a device enclosing program code to provide feedback elimination.

BRIEF DESCRIPTION OF THE DRAWINGS

These and other features, aspects, and advantages of the present disclosure will become better understood with regard to the following description, appended claims, and accompanying drawings wherein:

DETAILED DESCRIPTION OF THE DISCLOSURE

Figure 1:
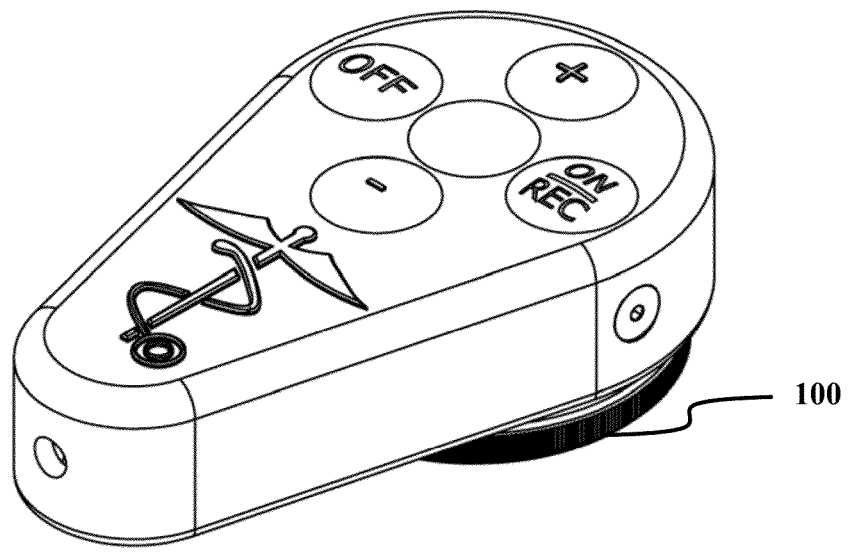
FIG. 1 presents an illustrative perspective view of an electronic stethoscope pick-up head according to one embodiment of the disclosure.

The present disclosure, in one embodiment, provides an electronic stethoscope that includes a pick-up head and a separate monitoring system. The pick-up head can be used on the body surface of a patient for collecting vibration and convert it to an electronic signal, which signal is then transmitted, either through a cable or wirelessly, to the monitoring system. The monitoring system can then display the vibration visually and/or broadcast the vibration as a sound signal, such as through a speaker or earphone. Such a design can avoid or reduce cross-infection between patients seen by the same clinician as each patient can have a separate pick-up head.

Further, the design of the pick-up head of the disclosure, in one embodiment, leads to reduced ambient noise and enhanced sensitivity to signal. In one aspect, the pick-up head includes a microphone that is placed in the chamber of the pick-up head, which is acoustically detached from the diaphragm on the pick-up head for picking up the vibration from a patient.

In another aspect, the chamber of the pick-up head includes an air path (vent) that allows air communication between the interior (microphone) and the exterior of the chamber. The air path is suitably chosen to restrict air flow to increase signal pick-up and reduce ambient noise. For instance, it is discovered that when the vented area is between about 1 $mm^2$ and 6 $mm^2$, the best result is achieved. Not only size, but the shape and length of the air path can also be adjusted to achieve such a result, as further described below.

Venting of the auscultation chamber is important to prevent the microphone from experiencing too much pressure and clipping the sound, which can significantly affect quality. The issue is that once the air space is vented, it provides a direct path for ambient noise to be picked up by the microphone. It is discovered that by introducing a convoluted air path (for example around the threads of a loosened screw), the present inventors were able to obtain the proper microphone sensitivity while muffling ambient noise. Such a screw setup, further, can also allow easy tuning of ventilation. As shown herein, different ventilation may be needed under different settings to achieve the best result.

Positioning of the microphone inside the auscultation piece was also tested. In one aspect, a "non-contact" microphone is used, in which the microphone can be placed anywhere along the traditional audio path. The term "non-contact" as used herein, refers to a microphone that does not generate an electronic signal by directly contacting the vibration source; rather, the vibration is transmitted to the microphone through air. It was discovered, unexpectedly, that fairly high quality reproduction of auscultation sounds was possible when the microphone was placed as far back as at the end of an 8' section of stethoscope tubing. However this positioning creates a large surface area that is capable of channeling ambient noise and incidental sounds of the tube bumping. By placing the microphone inside the auscultation piece, the surface area of the air cavity is reduced and thus this setting reduces the opportunity for ambient noise and contact noise to reach the microphone.

Further enhance of quality of the pick-up head can be achieved by adopting a noise-cancelling microphone. Such a microphone can reduce the effect of ambient noise. "Noise-cancelling" microphones have a small hole on the back of the microphone body which allows far-field acoustic pressure to act on both sides of the transducer body, effectively eliminating their effect from the acoustic signal. It is noted that these types of microphones rely on passive noise cancellation rather than the active noise cancelling technologies used in headphones.

Yet another contemplated feature is to eliminate feedback noise. Due to the proximity of the auscultation piece microphone to the base station speakers, the conventional system is capable of generating very large amounts of feedback. To address this issue, the following solutions can be adopted.

First, a feedback elimination hardware can be used. In this respect, notch filters can be used which are tuned with 1/60th octave precision and adjustable bandwidth to attenuate specific frequencies which cause feedback. This can be implemented using off-the-shelf sound processing hardware. In addition to the feedback elimination hardware, a low pass filter to eliminate high frequency sounds can be used that does not provide diagnostic value. This allows for the reduction of the number of feedback frequencies which require notch filtering.

Yet another approach involves the use of "microphone enable" button. The majority of feedback occurs in the configuration where the diaphragm is exposed to ambient air (not on skin). With a "microphone enable" button, the user can easily mute the system by releasing the enable button when the diaphragm is not being applied to the skin. This can dramatically increase the level of amplification that can be achieved before feedback is heard.

Further contemplated is a sound-processing method and delay hardware that adds a delay to signals generated by the transducer. Accordingly, an adjustable delay can be added to cause a slight delay of the "live" sound such that sounds reach the audience at the right time. By adding a delay it helps reduce the speed at which the feedback occurs. A 300 millisecond delay has been tested and is promising. Shorter delays are also contemplated.

By virtue of the "separate" pick-up head and monitoring system design, the system of the present disclosure can achieve functions that the conventional stethoscope cannot. For instance, such a system has the ability to dictate notes to recordings made using separate microphones at a base station. Also, it has the ability to change playback speed, pitch, volume, filter the sound, and save for comparison with future sounds.

Yet another contemplated feature is the ability to apply filters after recording sound. System will record the raw sounds and apply filtering only after playback, allowing the user to reconfigure the same recording to highlight different types of sounds. Still, another ability is to sample the ambient noise and adjust filtering to eliminate ambient ICU sounds. This is possible because the unit stays in a fixed position in the room in one example. It can also include a function that, when pressed, "learns" the ambient noise frequencies that are being transmitted through the auscultation piece.

Still further, the system can be configured to have the ability to turn loudspeaker on/off by analyzing the acoustic signal and deciding if the signal is characteristic of body sounds. Dual microphones (one inside the auscultation piece and one on the exterior of the auscultation piece) are also contemplated, to perform "active" noise cancellation by electronically comparing the two signals.

The electronic stethoscope pick-up head of the present disclosure can hook up directly (or wirelessly) to a speaker and display system, and hangs bedside. In such a way, the clinician need not break isolation to use the stethoscope; he or she can both hear and see the sounds on the wall unit; all healthcare providers on the team can listen and see the results at the same time, so the stethoscope need only be used once per visit. There is no reason for the clinician to use his or her own stethoscope, and no reason to avoid this step of the exam. The disposable tubing, and possibly the diaphragm piece, of the present disclosure is changed for every patient, so one method of hospital-acquired infection is eliminated. The devices described in this disclosure are also very user-friendly, allowing the clinician to perform the auscultation effortlessly and in a manner of seconds. It also allows for the possibility that a clinician or other provider record the sounds that are then played back during clinician rounds.

The sound data is played over a speaker, as well as displayed on a monitor bedside. Software may be provided in the base unit for analyzing the bodily sounds and make a diagnosis, much like an EKG machine. The processed sounds, in the form of electronic signals, can be easily recorded, and uploaded to electronic medical records for later review and archiving. The many benefits of these include improving the quality of healthcare, reducing the cost, saving time, and even improving teaching. In one embodiment, the system automatically saves the sounds when the system recognizes that sounds are being recorded. As each disposable piece is specific to a patient, these sounds could be automatically uploaded into an electronic medical record, or just saved locally.

Additional benefits that may be realized by the present disclosure include: a reduction in ambiguity regarding whether a current exam result is better or worse than a previous one, as reliance on a different clinician's analysis is no longer necessary—a patient's current clinician can just refer back to the stored audio or visual file, or software report. Telemedicine is another benefit of the present disclosure. For example, a clinician could perform the exam, and another clinician would then be able to review the audio later from either his or her office or at some other remote location.

Moreover, use of expensive, time-consuming tests that often have deleterious side effects can be reduced or even eliminated. For example, there may be specific borderline situations in which a clinician currently would send for an ECHO or CT Scan "just to be sure," which they may not feel the need to do when the electronic stethoscope of the present disclosure makes the stethoscope exam more reliable. This will result in a reduction in time, cost, and side effects (such as radiation from CT).

In some embodiments, the stethoscope pick-up head can include disposable parts, such as the diaphragm. In such embodiments, the other pars (e.g., base, chamber) do not need to be disposable so the pick-up head can be replaced with new parts to reduce infection at a low cost. In some embodiments, germ-resistant materials can be used. In some embodiments, the pick-up head can be placed in a germ-killing environment (e.g., UV light) when not in use.

The ability of the stethoscopes of the present disclosure to achieve high quality sound is unexpected. It should be readily appreciated by those trained in the art that it would be difficult to make quality sound over a speaker, due to both ambient noise and feedback, especially without the earpieces that greatly cutout ambient noise. This is even more evident in an intensive care unit (ICU). There was yet another challenge to make hand pieces with lower costs, as the contact microphones typically used in electronic stethoscopes now commercially available produce higher-quality sound but are very expensive. A low cost hand piece allows for the possibility of hand pieces that are disposable between patients, even further reducing the stethoscope's role in hospital acquired infection.

Figure 2:
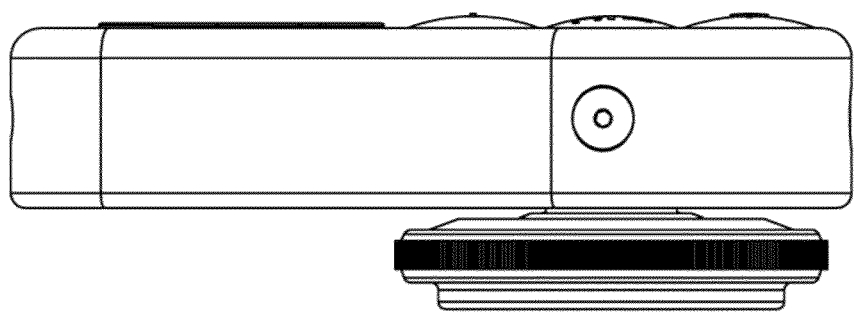
FIG. 2 presents an illustrative elevation side view of an electronic stethoscope pick-up head according to one embodiment of the disclosure.

FIGS. 1-2 illustrate a stethoscope pick-up head (an auscultation head) dimensioned to comfortably fit in a clinician's hand. Several controls may be disposed on a top surface of the pick-up head positioned with easy access of the controls to a clinician's fingers. The illustrated pick-up head includes thin diaphragms, microphone devices, or other devices capable of detecting a patient's bodily sounds.

The pick-up head can be provided in multiple shapes and sizes depending on the particular use, such as pediatric versions, veterinarian versions, etc, or adapted for providing Doppler functionality to allow auscultation of arterial blood flow or fetal heart beat. An ultrasound version is also envisioned, which includes an ultrasound transducer for emitting and receiving ultrasound signals. Moreover, the auscultation portion may come equipped with a magnet for detecting metal within a patient's body, such as foreign objects and medical devices—for example, ICDs, pacemakers, indwelling catheters, stents, feeding tubes, intubation tubes, nasal gastric tubes, etc.

Figure 3:
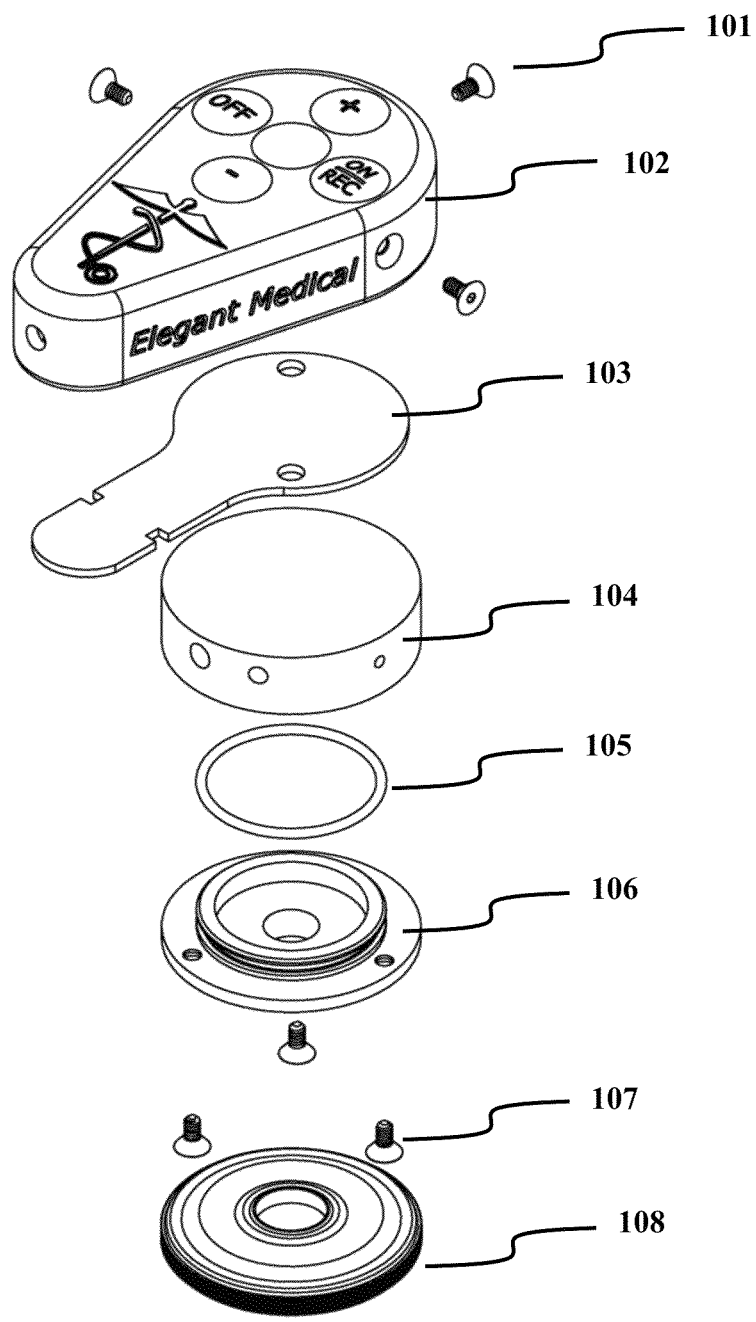
FIG. 3 shows each component that can be assembled to produce an electronic stethoscope pick-up head according to one embodiment of the disclosure.
Figure 4:
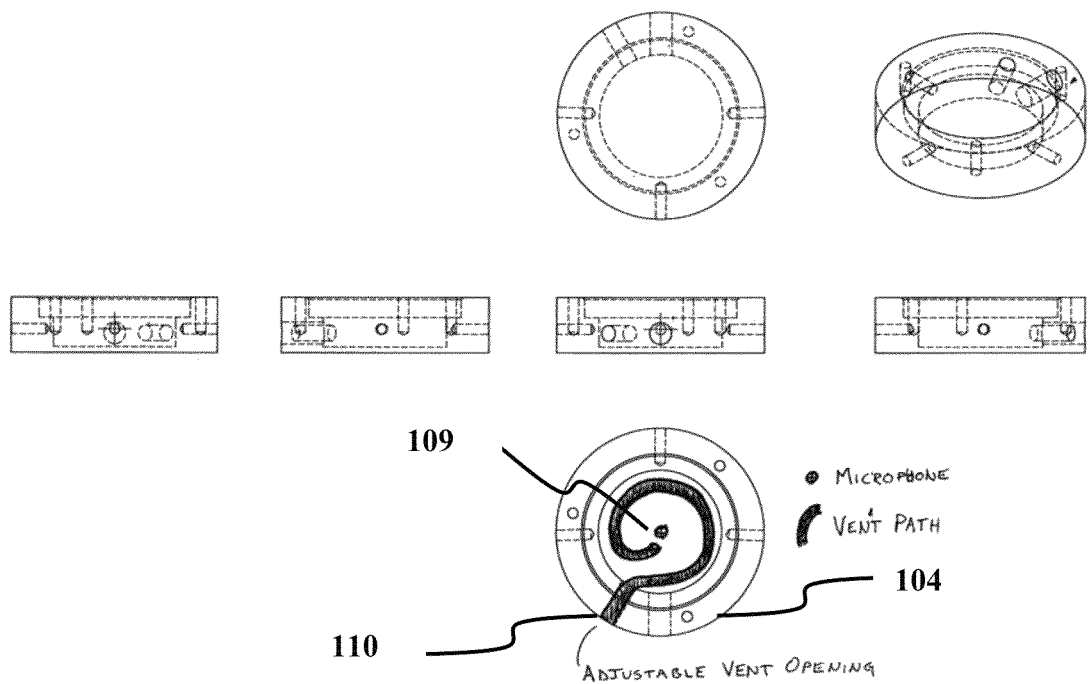
FIG. 4 illustrates a convoluted air path suitable for preparing an electronic stethoscope pick-up head according to one embodiment of the disclosure.

As more apparent in FIGS. 3-4, the pick-up head, in one embodiment, includes an acousto-electrical transducer (e.g., a microphone 109) disposed in a chamber (104), the transducer being configured to generate an electrical signal representing acoustical vibrations, wherein the chamber further comprises a sound influencing bell (FIG. 1, 100) defining a cavity to provide air communication between the transducer and a diaphragm attached to an outer end (108) of the bell, wherein the diaphragm is acoustically decoupled from the transducer (or, alternatively, the diaphragm is acoustically coupled to the transducer through air); and one or more ventilation air paths (110) as the only means to provide air communication between the cavity and outside of the chamber, wherein the air path is configured to restrict air flow through the air path.

FIG. 3 also illustrates how a pick-up head, of one embodiment of the present disclosure, can be made. It is noted that not all components as shown in FIG. 3 are required for the production of the pick-up head, and each of those components is not necessarily separable from another. In one embodiment, the pick-up head includes a case (102), a flat base scaffold (103) which can include an electronic circuit board, a chamber unit (104) a chamber sealer (106), a sealing o-ring (105) between the chamber unit and the sealer and a sound influencing bell (108). Further, screws including (101) and (107) are used to assemble these components, and can optionally be used to create ventilation air paths.

On the top surface of the case, there can be buttons which are electronically connected to the microphone or the external control or monitoring system. Such buttons can be used to power on or off, mute, or increase or decrease the electronic signal generated by the bodily sound or vibration. Optional other buttons include save, playback at different speeds, adjust pitch, playback old sounds or standardized sounds.

Figure 5:
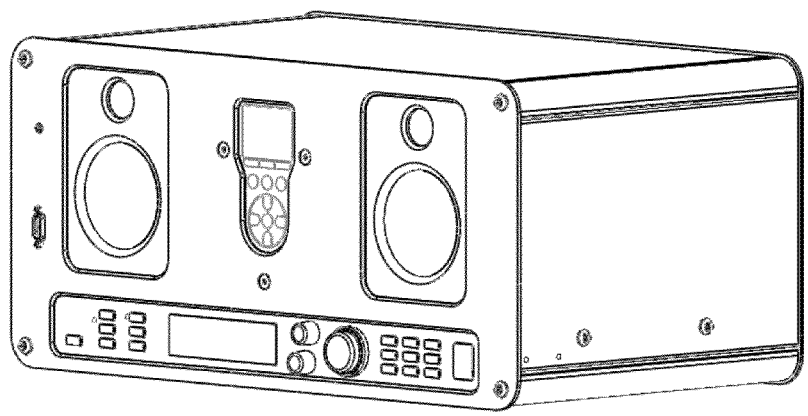
FIG. 5 shows an external unit having a speaker and display for use along with an electronic stethoscope pick-up head according to one embodiment of the disclosure.

Optionally, the pick-up head can include an outlet for connecting a cable to a monitoring or control unit (e.g., FIG. 5). Alternatively, the pick-up head can include a wireless transmitter for transmitting the electronic signal to an external monitoring or control unit. The wireless transmitter can be a Bluetooth or near field communication (NFC) transmitter, without limitation.

One approach to restrict air flow between the chamber (where the transducer is located) and the external space is to limit the internal size (diameter or cross-sectional area) or length of the path between the chamber and the external space.

For instance, in one embodiment at least a portion of the air path has a cross-sectional area of less than about 7 mm$^2$, or alternatively, less than about 2 mm$^2$, 2.5 mm$^2$, 3.5 mm$^2$, 4 mm$^2$, 5 mm$^2$, 6 mm$^2$, or 7 mm$^2$. In another embodiment, the cross-sectional area is greater than about 0.5 mm$^2$, or alternatively greater than about 0.1 mm$^2$, 0.2 mm$^2$, 0.3 mm$^2$, 0.4 mm$^2$, 0.6 mm$^2$, 0.7 mm$^2$, 0.8 mm$^2$, 0.9 mm$^2$, or 1 mm$^2$. In a particular aspect, the cross-sectional area is between about 1 mm$^2$ and about 2 mm$^2$. In one aspect, the area is between about 1 mm$^2$ and about 2 mm$^2$. In another aspect, the area is between about 4 mm$^2$ and 6 mm$^2$.

In another aspect, at least a portion of the air path has a diameter of less than about 4 mm, or alternatively less than about 1.6 mm, 1.7 mm, 1.8 mm, 1.9 mm, 2.1 mm, 2.2 mm, 2.3 mm, 2.4 mm, 2.5 mm, 3 mm, or 3.5 mm. In yet another aspect, the diameter is greater than about 0.8 mm, or alternatively 0.35 mm, 0.4 mm, 0.5 mm, 0.6 mm, 0.7 mm, 0.8 mm, 0.9 mm, 1 mm, 1.1 mm or 1.2 mm.

In some aspects, the cross-sectional size of the air path is adjustable. Such adjustability can be achieved, for instance, by using one or more screws which can be loosened or tightened. Alternatively, an elastomeric venting tube can be used where the clinician can pinch the tube to affect the vent area. Yet in another aspect, a spring loaded valve can be used where the clinician can push a button to change the vent area. In still another aspect, a thin slit opening can be used, allowing the clinician to change the vent area by positioning their finger in different locations. It is contemplated that the adjustment can be continuous or discrete. For discrete adjustment, an inner ring and outer ring, for instance, can be used such that, when twisted, reveals an additional small hole that increases the venting surface area.

In some aspects, the air path is convoluted. The term "convoluted" refers to a path that is not straight, or alternatively a path for which the direct distance between both of its ends is substantively (e.g., 1.5, 2, 2.5, 3, 3.5, 4 or 5 fold) shorter than the total length of the path (see illustration in FIG. 4).

Acousto-electrical transducers are known in the art. In one aspect, the transducer comprises a microphone. In another aspect, the transducer comprises an electromagnetic diaphragm.

In some aspects, the pick-up head further provides a flexible material for affixing the transducer in the chamber and separating the transducer from other parts of the chamber to reduce noise. In some aspects, the pick-up head or the external system connected to the head includes a device enclosing program code to provide feedback elimination.

FIG. 5 illustrates an external control/monitoring system (a "base unit") for the pick-up head. The base unit can include a loudspeaker for broadcasting audio corresponding to bodily sounds picked up by the pick-up head. The loudspeaker allows multiple clinicians to listen to the bodily sounds picked up by the auscultation portion simultaneously. Additionally, the base unit includes a display, which displays diagnostic representations of the bodily sounds, allowing clinicians to visually evaluate the sounds.

The base unit contains an acoustic signal processing circuit for converting the audio waves received by the pick-up head into electronic representations. The electronic representation can then be further processed for display on the display and evaluated by diagnostic software capable of making diagnoses suggestions. For example the system would be able to judge a heart sound as a III/VI mitral valve murmur.

Further, the base unit may be equipped with a user interface (not shown), such as a touch screen overlay on the display, or keyboard and pointing device. In one example, the user interface allows a healthcare worker to identify the patient being examined, which part of a patient's anatomy is being examined (e.g. heart, which part of heart, or lung, which quadrant of lung), time and date, other diagnostic devices being used, etc.

The controls may also be configured to provide user inputs to the base unit, and in fact, this option may be preferable as it eliminates the need for the clinician to touch anything other than the pick-up head. This information is saved along with the sound and video files. These files are downloadable onto computer media, saved in speaker/display, or uploaded into medical records. The base unit is further equipped with controls for allowing a clinician or healthcare worker to select different frequency and/or amplitude ranges for the sounds to be displayed.

The base unit can be equipped with prompts requiring the healthcare worker to provide information regarding where each step of the exam is being done. For example, it may ask that the healthcare worker first put the diaphragm on the right sternal border, and then a few moments later move it to the left sternal border, etc. It can prompt for bell vs. diaphragm use. For lung examinations, the prompts may request different lung fields. In this way, a stethoscopic examination can be carried out in a very controlled and uniform manner, reducing the chance that a particular area of interest is not examined. The prompts may be presented either on the display or by way of speech synthesis Also, the base unit can be configured to store voice annotations from the examining healthcare worker along with the stethoscopic sounds. In this way, notes regarding the examination can remain associated with the recorded stethoscopic sounds. By saving such exams, future healthcare workers will have data to refer to as a baseline, to see if patient conditions have worsened or are stable.

The base unit may be wall mounted, attachable to a patient's bed, built into the patient's bed, free-standing, incorporated with other bedside monitors, remotely located, portable, and mountable in an ambulance. The base unit may further provide connectors for storage media such as SD cards, MM cards, flash drives, etc. for downloading examination data and reports from the base unit 104. This interface may also be configured to allow for the uploading of audio files as well as for updating firmware, etc.

Additionally, the base unit may be networkable, i.e., connectable to a hospital's local area network, wide area network or the Internet, allowing remote users to receive data from the base unit. Further in being coupled to the network, the based unit allows the examining healthcare worker to retrieve information through the base unit, such as patients records stored at an in-hospital database server or from other hospitals that may have provided treatment to the patient.

The base unit may come equipped with headphone jacks to allow a healthcare worker to plug in a pair of headphones in situations such as emergency rooms where the noise level may make it difficult to properly listen to the stethoscopic sounds broadcast by the loudspeaker, or in situations where there is a risk of disturbing nearby patients. Wireless headphones may also be usable with the base unit by providing a wireless transmitter adapted for connecting to wireless headphones.

Through the improvements to the conventional stethoscope provided by the present disclosure, increase in its use, and standardization of the physical diagnosis through software interpreters and ability to save data, the present disclosure may reduce the number of needed "further tests" such as echocardiograms and high-resolution CT scans, particularly in borderline cases. For example, if a patient were found to have a heart murmur in 2006, and given an echocardiogram. Three years later, a new clinician examining the patient hears a heart murmur, and looking through the records sees that the patient had an echocardiogram. However, this clinician may not be able to tell if the murmur has become worse—as he can only compare his own interpretation of the exam with that jotted down by the first clinician. However, had the first stethoscope exam by the first clinician been done with the electronic stethoscope of the present disclosure, the degree of murmur would have been standardized, and the sound and display files may even be available for review. A repeat echocardiogram may not be necessary.

Similar scenarios often occur with lung sounds and High Resolution CT scans, which are not only expensive and time intensive tests, but also expose the patient to a large amount of radiation and contrast dye, both of which carry significant risks to the patient.

On the other side of the coin, the stethoscope of the present disclosure will decrease the amount of missed diagnoses, as less trained healthcare workers are more likely to catch remarkable findings of the physical exam when stethoscope-received sounds are played over a speaker, displayed on a screen, and analyzed with software.

For the same reason, the present disclosure will be usable as a training aid for healthcare workers to hear the differences in stethoscope sounds, as the software will analyze and tell the healthcare worker what they are hearing.

Furthermore, as the sound is played over a speaker and displayed visually, it will be unnecessary for each member of a clinician's team to listen with his or her own stethoscope, saving time bedside, as well as saving the patient the hassle of having each member of the team touch him or her.

Since the stethoscopic sounds are saved electronically as a sound file and a video file, the system of the present disclosure can prove extremely valuable in the increasing use of "telemedicine," which allows clinicians to review sounds of a patient before even meeting the patient, while now the clinician may only be able to review medical records, medical images, etc.

Moreover, the telemedicine applications of the present disclosure may provide a significant upgrade in the quality of medical service available in remote places, such as mobile medics in the $3^{rd}$ world; space stations; polar stations; submarines; cruise ships.

The present disclosure may include pre-saved standard sounds for review, such as "normal" heartbeat, and specific pathologic sounds (lung sounds, abdominal sounds, etc). This feature may be incorporated into a "learning mode" as well, with exercises and demonstrations to increase a clinician's or healthcare worker's ability to detect and distinguish specific pathological sounds. For example, normal active bowel sounds signal that the gut is starting to work again after having surgery. No bowel sounds or high-pitched sounds are consistent with a bowel obstruction. Being able to properly distinguish between these sounds may greatly impact a patient's recovery time.

Additionally, contemplated is a system in which continuous monitoring or listening to sounds, with thin and comfortable auscultation pieces that are continuously in contact with the patient. This could have applications throughout medicine, a few examples include: use during surgery where the auscultation piece may reach where a clinician cannot reach during surgery due to patient positioning and sterile field; or on the lungs of patients who are receiving intravenous fluids to pick up early on signs of pulmonary edema; or applications in home setting or nursing home setting for those with congestive heart failure who have many visits to the hospital, to pick up early on signs of pulmonary edema and intervene early to avoid the ER visit and likely hospitalization. It is further contemplated that the system can be used for titration of fluids in patients having congenital heart failure or end stage renal disease. In one embodiment, there may be automatic titration as the rales and respiratory rates are tracked.

EXPERIMENTAL EXAMPLES

Example 1

Objective Testing of the Electronic Stethoscopes

This example was designed to subjectively and objectively evaluate the performance of various configurations of the electronic stethoscope pick-up head. The objective testing was accomplished through analysis of sound levels recorded through the auscultation piece. Subjective testing gathered observations and opinions from medical clinicians using the stethoscope to listen to heart and lung sounds.

Figure 6:
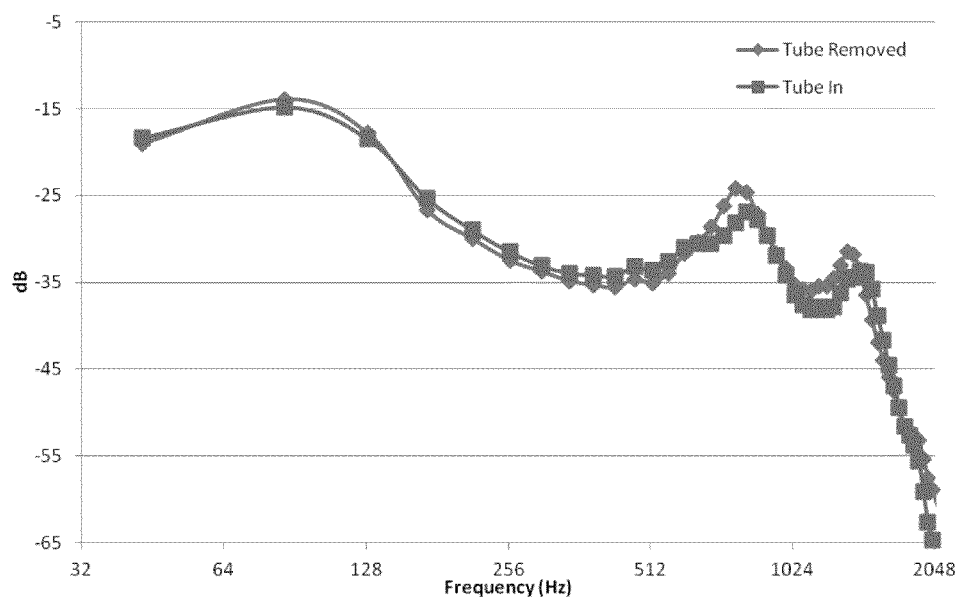
FIG. 6 presents a chart showing the effect of a tube installed in an electronic stethoscope pick-up head according to one embodiment of the disclosure.

Test Equipment
  Specialized testing equipment included the following:
  1. Behringer UF0202 Audio to USB converter
  2. "Stethospeaker": A normal stethoscope head with a headphone speaker sealed into it. This turns the stethoscope head into a speaker that fits the auscultation piece.
  3. Elegant Medical Base Station
    a. Tascam DR-40 Linear PCM Recorder
    b. Behringer UltraCurve Pro
    c. AudioEngine Speakers
  4. Elegant Medical Auscultation Piece Testes Performed
Microphone Position
  Purpose:
  Determine the most effective position of the microphone within the auscultation piece
  Setup:
  The microphone resides in a "sound chamber" in the auscultation piece which is a cylindrical chamber connected to the diaphragm chamber. The microphone was placed in various configurations within the chamber and various sample noises were played through the stethospeaker.
  Configurations Tested:
  1. Chamber empty, except venting tubes. Microphone "floating" in chamber.
  2. Aluminum tube inserted into chamber, completely surrounding the microphone. Microphone is touching ID of tube. Tube is coupled to venting system and diaphragm chamber with silicone.
  Results:
  As shown in FIG. 6, the tube was not found to have a significant effect (>3 dB) for most of the range of frequencies of interest for heart and lung sounds (20 Hz-2 kHz). In the small peaks where the effect is significant, the condition with the tube removed performed better.

Sound Chamber Venting
  Purpose:
  Determine the optimal size of the auscultation chamber vent system opening.
  Setup:
  The Auscultation piece sound chamber can be "vented" such that the system is not air-tight and there is a path to ambient air. In general, a smaller vent seems to capture sound better, but too small of a vent will overpower the microphone that we're using, giving a "clipped" sound. Too much venting, however, allows the microphone to pick up ambient noise which both adds to the general noise of the system, as well as providing a path for direct audio feedback.
  Configurations Tested:

| | | |
|---|---|---|
| 1. | Vented area: ~6.00 mm$^2$ | [Test + Main Vent] |
| 2. | Vented area: 3.94 mm$^2$ | [Test Vent] |
| 3. | Vented area: ~2.00 mm$^2$ | [Main Vent] |
| 4. | Vented area: 1.72 mm$^2$ | [Test Vent + Small Allen Key] |
| 5. | Vented area: 0.54 mm$^2$ | [Test Vent + Big Allen Key] |
| 6. | Vented area: 0.00 mm$^2$ | [All vents closed] |

Figure 7:
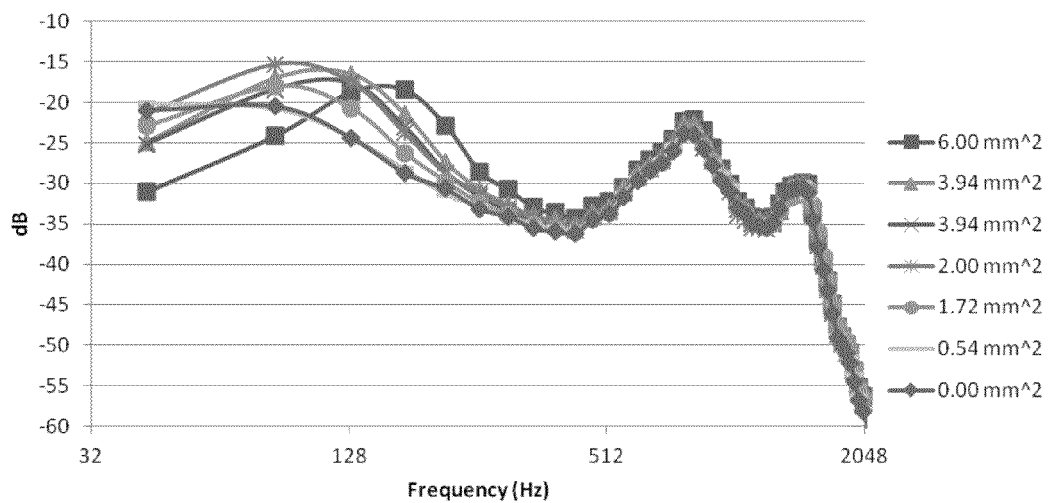
FIG. 7 presents a chart showing the impact of different sizes of vented areas, in terms of microphone response, on an electronic stethoscope pick-up head according to one embodiment of the disclosure.
Figure 8:
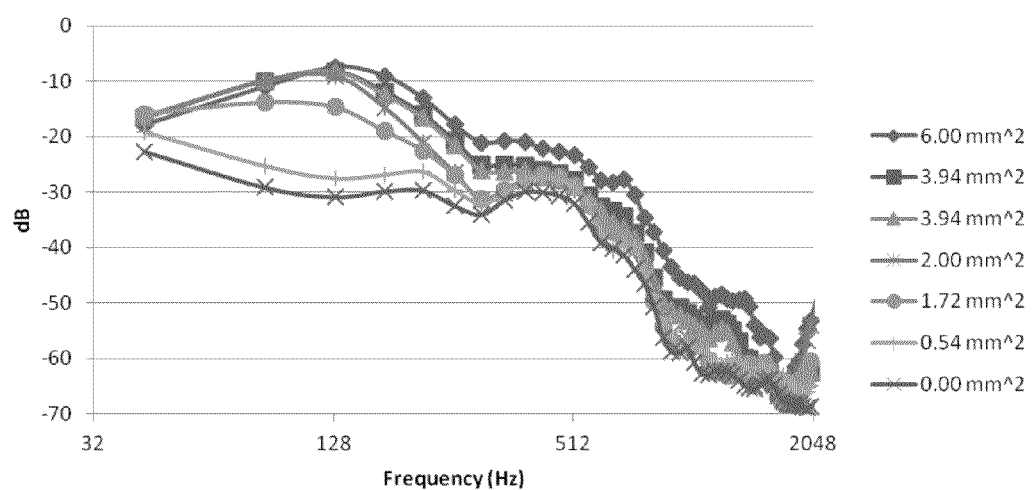
FIG. 8 presents a chart showing the impact of different sizes of vented areas, in terms of ambient noise capture, on an electronic stethoscope pick-up head according to one embodiment of the disclosure.

Results:
  Based solely on these two graphs shown in FIG. 7-8, the minimal venting cases seem best, however in practical testing it was found that the two smallest venting cases (0.00 and 0.54) were overpowering the microphone and distorting (clipping) the sound. Therefore, the optimal vent size range is between 1 mm² and 2 mm².

This testing has also shown that manipulating the size of the vent can amplify or attenuate sounds in specific frequency ranges. For example, when ranking performance of vent sizes in FIG. 8, it can be seen that the best performers at 40 Hz are the worst performers at 200 Hz. This opens up the possibility of using the vent configuration to preferentially amplify sounds that are specific to a particular stethoscope exam (heart vs. lung).

Example 2

Subjective Testing of the Electronic Stethoscopes

In order to solicit expert opinion, this example surveyed medical clinicians with varied backgrounds for rating their preferences for different configurations of the system.

Venting

Purpose:

Same as venting test described in Example 1.

Setup:

Similar to the objective test for venting, as described Example 1, the auscultation piece was placed in one of the following configurations:

| | | |
|---|---|---|
| Condition 1: | Vented area: ~6.00 mm² | [Test + Main Vent] |
| Condition 2: | Vented area: 3.94 mm² | [Test Vent] |
| Condition 3: | Vented area: 1.72 mm² | [Test Vent + Small Allen Key] |
| Condition 4: | Vented area: 0.54 mm² | [Test Vent + Big Allen Key] |
| Condition 5: | Vented area: 0.00 mm² | [All vents closed] |

A test subject was used to generate heart and lung sounds, and the participants were asked to rate the quality of those sounds in both using the speaker and the headphones.

Participants were asked to compare two conditions at a time. Starting with the fully open vent condition, the participants were asked for their preference for condition 1 or 2, then 2 or 3, etc. If neither condition was preferable, they were allowed to select "equivalent".

Results:

While the clinicians did not all have the same preferences, there was a general preference for the more vented configurations (conditions 1 & 2). As the vent size was reduced, the clinicians noted that there seemed to be more rattling and the sound was less crisp. The following table shows the most preferred configuration for each test.

| | Heart Sounds | Lung Sounds |
|---|---|---|
| With Headphones | Configuration 2 | Configuration 2 |
| With Speaker | Configuration 2 | Configuration 1 |

Microphone Positioning

Purpose:

Same as positioning test described in Example 1.

Setup:

The electronic stethoscope was used in the standard venting condition (condition 3 from Example 1). Volume was set as high as possible without encountering feedback.

Heart sounds from a live subject were played through the speakers in two configurations. Sounds were recorded because of the length of time required to change configurations. Participants were able to listen to the live sounds, and were asked to compare between the two recorded sounds played one after another.

Configurations Tested:
1. Chamber filled with silicone. Microphone embedded in silicone.
2. Aluminum tube inserted into chamber, completely surrounding the microphone. Microphone is touching the inner wall of the tube. Tube is coupled to venting system and diaphragm chamber with silicone.

Results:

The clinicians were unanimous in saying that they could not tell a difference between configuration 1 and 2, As a result, the device can be flexibly engineered according to multiple configurations while still seeing beneficial results and sound clarity.

Comparison to Existing Stethoscopes

Purpose:

Answer the following questions:
1. Is the Elegant Stethoscope system able to provide diagnostic quality sound in both the speaker and headphones setup?
2. Is the sound (both speakers & headphones) comparable to the ThinkLabs from the standpoint of being able to diagnose a patient?

Setup:

Heart and lung sounds from a live test subject were played for the clinicians in the configurations described above.

The ThinkLabs Rhythm:ds32a Stethoscope has an audio line-out that was plugged directly into the speakers or headphones. The ThinkLabs Stethoscope was used in the "amplified" condition with the volume at 10 out of 10, except in the cases where the clinicians preferred a lower volume level.

The stethoscope used in the standard venting configuration corresponded to condition 3 from Example 1. Volume was set as high as possible without encountering feedback.

Results:

The clinicians were unanimous in the following responses:

| | With Headphones | With Speaker |
|---|---|---|
| Is the Elegant Stethoscope system able to provide diagnostic quality sound? | Yes | Yes |
| Is the sound comparable to the ThinkLabs from the standpoint of being able to diagnose a patient? | Yes | Yes |

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

The invention claimed is:

1. An apparatus comprising:
   a chamber having an interior and an exterior, the chamber including one or more ventilation air paths configured to provide first air communication between the interior and the exterior of the chamber, the one or more ventilation air paths being further configured to restrict air flow through the one or more ventilation air paths;
   a non-contact acousto-electrical transducer disposed in the interior of the chamber, the transducer being configured to generate an electrical signal representing acoustical vibrations;

a sound influencing bell formed as part of the chamber and defining a cavity;

a diaphragm coupled to an outer end of the bell, the cavity of the bell being configured to provide second air communication between the transducer and the diaphragm, and the second air communication acoustically coupling the diaphragm to the transducer.

2. The apparatus of claim 1, wherein the transducer comprises a microphone.

3. The apparatus of claim 1, wherein the transducer comprises an electromagnetic diaphragm.

4. The apparatus of claim 1, further comprising a cable for connecting the transducer to an external device.

5. The apparatus of claim 4, wherein the external device is a speaker or an electronic screen.

6. The apparatus of claim 1, further comprising a wireless transmitter for transmitting an electronic signal generated by the transducer.

7. The apparatus of claim 6, wherein the wireless transmitter is a Bluetooth or near field communication (NFC) transmitter.

8. The apparatus of claim 1, further comprising a flexible material for affixing the transducer in the chamber and separating the transducer from other parts of the chamber.

9. The apparatus of claim 1, further comprising feedback elimination hardware to eliminate feedback noise.

10. The apparatus of claim 9, wherein the feedback elimination hardware includes notch filters and/or a low pass filter.

11. The apparatus of claim 9, wherein the feedback elimination hardware includes a transducer enable button that is configured to allow a user to turn off the transducer.

12. The apparatus of claim 9, wherein the feedback elimination hardware includes delay hardware that is configured to introduce a delay to signals generated by the transducer.

13. The apparatus of claim 1, further comprising a device enclosing program code to eliminate feedback noise.

14. The apparatus of claim 1, wherein the one or more ventilation air paths are further configured to provide the only means of air communication between the interior and the exterior of the chamber.

15. The apparatus of claim 1, wherein at least a portion of each of the one or more ventilation air paths has a cross-sectional area of less than about 6 $mm^2$.

16. The apparatus of claim 15, wherein the cross-sectional area is greater than about 0.5 $mm^2$.

17. The apparatus of claim 16, wherein the cross-sectional area is between about 1 $mm^2$ and about 5 $mm^2$.

18. The apparatus of claim 1, wherein at least a portion of each of the one or more ventilation air has a cross-sectional area that is adjustable.

19. The apparatus claim 1, wherein the one or more ventilation air paths are convoluted.

20. The apparatus of claim 2, wherein the microphone is a noise-cancelling microphone.

* * * * *